(12) United States Patent
Ellis et al.

(10) Patent No.: US 9,839,464 B2
(45) Date of Patent: Dec. 12, 2017

(54) DEVICE AND METHOD FOR USE DURING LIGAMENT RECONSTRUCTION

(71) Applicant: Smith & Nephew, Inc., Andover, MA (US)

(72) Inventors: Daniel B. Ellis, Holliston, MA (US); Michael C. Ferragamo, Foster, RI (US); Bryce Bederka, Portland, OR (US); Michael J. Perriello, Hopedale, MA (US)

(73) Assignee: Smith & Nephew, Inc., Memphis, TN (US)

( * ) Notice: Subject to any disclaimer, the term of this patent is extended or adjusted under 35 U.S.C. 154(b) by 735 days.

(21) Appl. No.: 14/215,654

(22) Filed: Mar. 17, 2014

(65) Prior Publication Data

US 2014/0316422 A1 Oct. 23, 2014

Related U.S. Application Data

(63) Continuation of application No. 13/050,520, filed on Mar. 17, 2011.

(Continued)

(51) Int. Cl.
*A61B 17/88* (2006.01)
*A61F 2/08* (2006.01)
(Continued)

(52) U.S. Cl.
CPC ........ *A61B 17/8897* (2013.01); *A61B 5/1076* (2013.01); *A61B 17/1764* (2013.01);
(Continued)

(58) Field of Classification Search
CPC . A61B 17/17; A61B 17/1703; A61B 17/1714; A61B 17/1721; A61B 17/1739;
(Continued)

(56) References Cited

U.S. PATENT DOCUMENTS 5,071,420 A 12/1991 Paulos et al.
5,122,146 A * 6/1992 Chapman ........... A61B 17/1717
606/102

(Continued)

FOREIGN PATENT DOCUMENTS

CN 2719254 Y 8/2005
DE 4016476 A1 11/1991

(Continued)

OTHER PUBLICATIONS

Notice of Reasons for Rejection for Japanese Patent Application No. 2013-500209 dated Jul. 13, 2015.

(Continued)

*Primary Examiner* — Kevin T Truong
*Assistant Examiner* — Tracy Kamikawa
(74) *Attorney, Agent, or Firm* — Burns & Levinson LLP; Joseph M. Maraia

(57) ABSTRACT

The present disclosure relates to a device for use during ligament reconstruction surgery. The device includes a handle and a shaft coupled to the handle, the handle including a first channel for housing of an insert, a second channel, a third channel for housing of the shaft, a first window, a second window, and a groove. A method for use during ligament reconstruction surgery is also disclosed.

14 Claims, 13 Drawing Sheets

Related U.S. Application Data

(60) Provisional application No. 61/315,228, filed on Mar. 18, 2010.

(51) Int. Cl.
*A61B 5/107* (2006.01)
*A61B 90/00* (2016.01)
*A61B 17/16* (2006.01)
*A61B 17/17* (2006.01)

(52) U.S. Cl.
CPC .......... *A61B 17/8869* (2013.01); *A61B 90/06* (2016.02); *A61F 2/0805* (2013.01); *A61B 17/1675* (2013.01); *A61B 17/1714* (2013.01); *A61B 2090/062* (2016.02); *A61B 2090/0811* (2016.02); *A61F 2002/0882* (2013.01); *A61F 2250/0097* (2013.01)

(58) Field of Classification Search
CPC .............. A61B 19/46; A61B 2019/461; A61B 2019/462; A61F 2/08; A61F 2/0805; A61F 2/0811; A61F 2002/0817; A61F 2002/0823; A61F 2002/0829; A61F 2002/0841; A61F 2002/0847; A61F 2002/0852; A61F 2002/0858; A61F 2002/0864; A61F 2002/087; A61F 2002/0876; A61F 2002/0882; A61F 2002/0888; A61F 2002/7615; A61F 2002/762

See application file for complete search history.

(56) References Cited

U.S. PATENT DOCUMENTS

| | | | |
|---|---|---|---|
| 5,139,520 A | | 8/1992 | Rosenberg |
| 5,180,388 A | * | 1/1993 | DiCarlo ............... A61B 17/17 606/102 |
| 5,403,321 A | | 4/1995 | DiMarco |
| 5,549,613 A | | 8/1996 | Goble et al. |
| 5,645,588 A | | 7/1997 | Graf et al. |
| 5,928,243 A | | 7/1999 | Guyer |
| 5,931,840 A | | 8/1999 | Goble et al. |
| 7,172,599 B2 | | 2/2007 | Steffensmeier et al. |
| 7,299,561 B2 | * | 11/2007 | Castaneda .......... A61B 17/1725 33/512 |
| 7,338,492 B2 | * | 3/2008 | Singhatat ............ A61B 17/1714 128/898 |
| 8,734,461 B2 | | 5/2014 | Ellis et al. |
| 2002/0133165 A1 | | 9/2002 | Whittaker et al. |
| 2003/0032865 A1 | | 2/2003 | Estes et al. |
| 2004/0029293 A1 | | 2/2004 | Nugent et al. |
| 2005/0085825 A1 | | 4/2005 | Castaneda |
| 2005/0187560 A1 | | 8/2005 | Dietzel et al. |
| 2006/0211953 A1 | * | 9/2006 | Zannis ................ A61B 5/1076 600/587 |
| 2008/0262555 A1 | | 10/2008 | Assell et al. |
| 2008/0306408 A1 | * | 12/2008 | Lo ...................... A61B 5/1076 600/587 |
| 2009/0022801 A1 | | 1/2009 | Vachon |
| 2009/0228015 A1 | | 9/2009 | Ellis et al. |
| 2009/0306675 A1 | | 12/2009 | Wong et al. |
| 2010/0145340 A1 | | 6/2010 | Phab et al. |
| 2011/0166607 A1 | | 7/2011 | Castaneda et al. |
| 2012/0109132 A1 | | 5/2012 | Ellis et al. |
| 2012/0330323 A1 | | 12/2012 | Lizardi et al. |
| 2013/0096566 A1 | | 4/2013 | Bowen et al. |
| 2013/0110120 A1 | | 5/2013 | Baroud et al. |
| 2014/0276884 A1 | | 9/2014 | Lizardi et al. |
| 2014/0296861 A1 | | 10/2014 | McCarthy et al. |

FOREIGN PATENT DOCUMENTS

| | | |
|---|---|---|
| EP | 0361756 A1 | 4/1990 |
| EP | 0556570 A1 | 8/1993 |
| EP | 2008585 A1 | 12/2008 |
| FR | 636447 A | 4/1928 |
| FR | 2901465 A1 | 11/2007 |
| WO | 9415556 A1 | 7/1994 |
| WO | 1994015556 A1 | 7/1994 |
| WO | 2005122921 A2 | 12/2005 |
| WO | 2008091690 A1 | 7/2008 |

OTHER PUBLICATIONS

Communication pursuant to Article 94(3) EPC from related European Application No. 11710640.1 dated Mar. 8, 2016.
First Office Action and Search Report for Chinese Application No. 201180014483.5, dated Jul. 8, 2014 (Note all references listed in search Report except for CN2719254 previously identified by Applicants.).
International Search Report and Written Opinion for PCT/US2011/028844.
International Preliminary Report on Patentability for International Application No. PCT/US2011/028844, dated Sep 27, 2012.
First Office Action for related Chinese Application No. 201180014483.5 dated Jul. 8, 2014.
Australian Patent Examination Report for Australian Patent Application No. 2011227190 dated Mar. 25, 2015.
International Search Report for related International Application No. PCT/US2014/031827 dated Jun. 24, 2014.

* cited by examiner

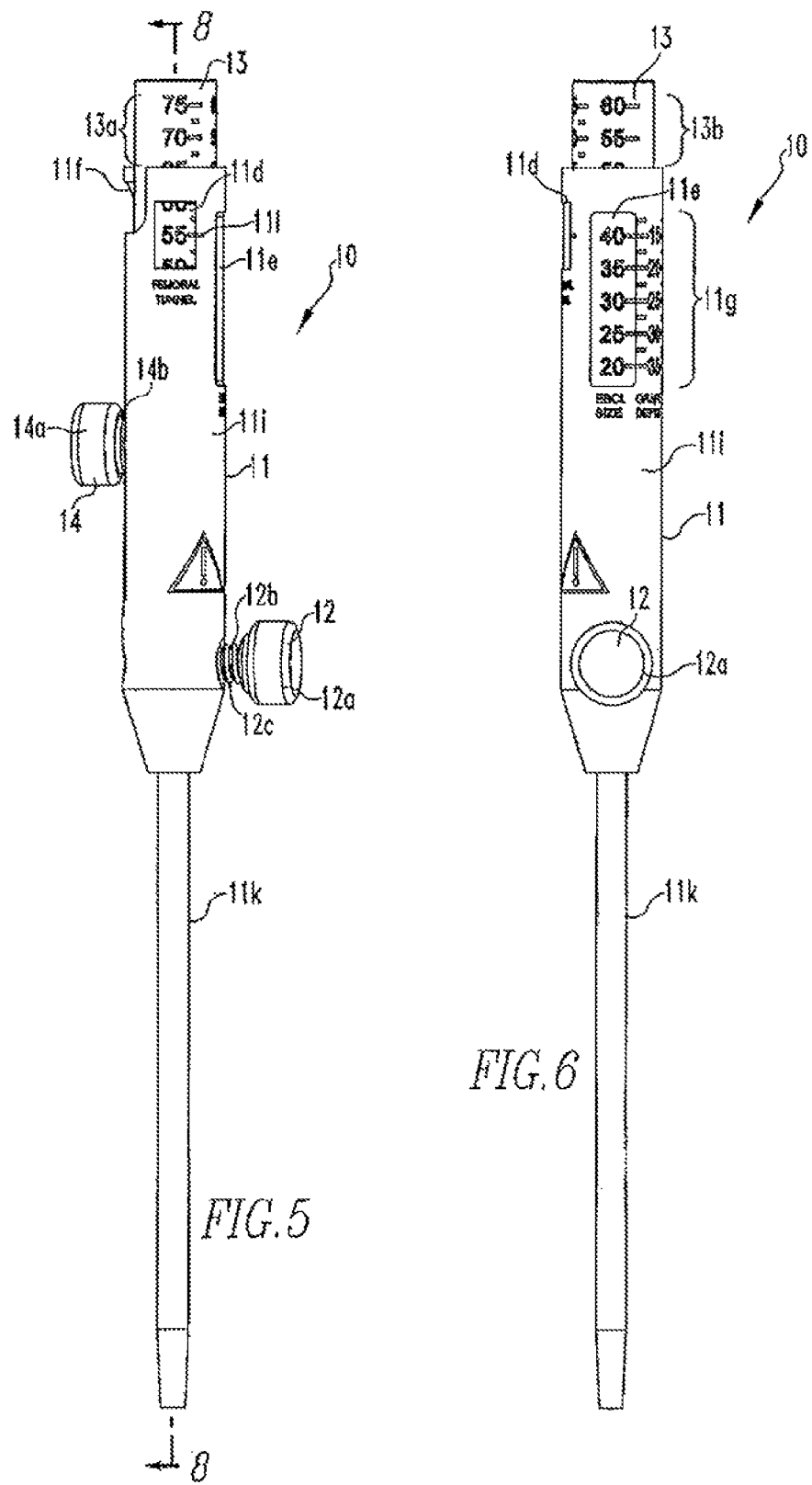

DEVICE AND METHOD FOR USE DURING LIGAMENT RECONSTRUCTION

CROSS REFERENCE TO RELATED APPLICATIONS

This application claims priority to U.S. patent application Ser. No. 13/050,520, filed Mar. 17, 2011 which claims the benefit of U.S. Patent Application Ser. No. 61/315,228, filed Mar. 18, 2010, the disclosure of which is incorporated herein in its entirety.

BACKGROUND

Field of Technology

The present disclosure relates to ligament reconstruction surgery, and more specifically, a device and method for determining lengths during reconstruction surgery.

Related Art

The creation of reconstruction tunnels in the femur for ligament reconstruction surgery is required for the attachment of a soft tissue graft, such as a semitendinosis tendon. The length of the femoral tunnel needs to be determined and calculations need to be made to, among other things, determine the appropriate lengths for the implants that are used to fixate the grafts in the tunnels. Currently, manual calculations are used. These manual calculations are often inaccurate and time consuming. Therefore, a device and method for more accurately making these calculations are needed.

SUMMARY

In one aspect, the present disclosure relates to a device for use during ligament reconstruction surgery. The device includes a handle and a shaft coupled to the handle, the handle including a first channel for housing of an insert, a second channel, a third channel for housing of the shaft, a first window, a second window, and a groove.

In an embodiment, the device further includes the insert, the insert including a first set of numbers for display through the first window, a second set of numbers for display through the second window, and a knob assembly disposed within the groove. In another embodiment, the insert further includes a nipple extending from an end of the insert.

In another aspect, the present disclosure relates to a method for use during ligament reconstruction surgery. The method includes placing a guide wire through a tibia and a femur; providing a device comprising a handle and a shaft coupled to the handle, the handle including a first channel housing an insert, a second channel, a third channel housing the shaft, a first window, and a second window; placing the device over an end of the guide wire; viewing a first set of numbers on the insert through the first window to determine a femoral tunnel length; viewing a second set of numbers on the insert through the second window to determine a femoral socket depth; creating a femoral socket; creating a through hole in the femur, the through hole extending from the femoral socket, the femoral socket and the through hole together creating the femoral tunnel; and placing a soft tissue graft within the femoral tunnel.

In an embodiment, the method further includes creating a tibial tunnel prior to placing the guide wire through the tibia and the femur. In another embodiment, the soft tissue graft is placed within both the femoral tunnel and the tibial tunnel. In yet another embodiment, placing the guide wire through the tibia and the femur includes aligning a laser ring on the guide wire with an end of the femur. In a further embodiment, placing the device over the guide wire includes contacting an end of the shaft with the femur. In yet a further embodiment, a number on the second set of numbers represents a length of a closed loop suture.

In an embodiment, viewing a second set of numbers on the insert through the second window to determine a femoral socket depth includes finding a number on a first set of numbers on the handle that corresponds with the number of the second set of numbers on the insert that represents the length of the closed loop suture. In another embodiment, the number on the first set of numbers on the handle represents a drill depth for the soft tissue graft. In another embodiment, the method further includes finding a number on a second set numbers on the handle that corresponds with the soft tissue graft drill depth number. In yet another embodiment, the number on the second set of numbers represents a drill depth for the femoral socket.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 5 shows markings visible from the side elevation of the insert;

FIG. 6 shows markings visible from the front elevation of the insert;

FIGS. 10 and 10a shows a guide wire insertable through the shaft of the device;

FIGS. 16 and 16a show insertion of a suture strand via the guidewire; and

DETAILED DESCRIPTION OF THE EMBODIMENTS

The following description of the preferred embodiment(s) is merely exemplary in nature and is in no way intended to limit the disclosure, its application, or uses.

Figure 1:
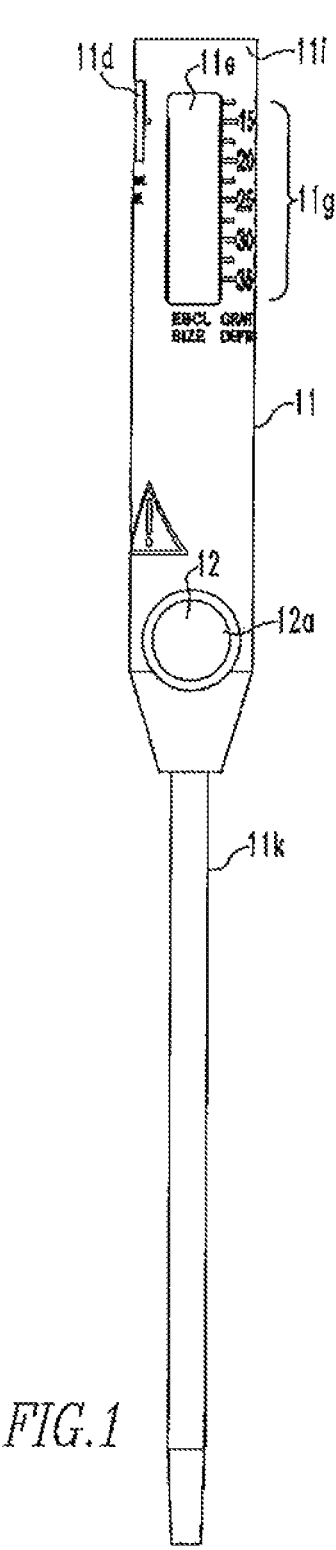
FIG. 1 shows a front elevation of the handle and shaft of the device of the present disclosure.
Figure 2:
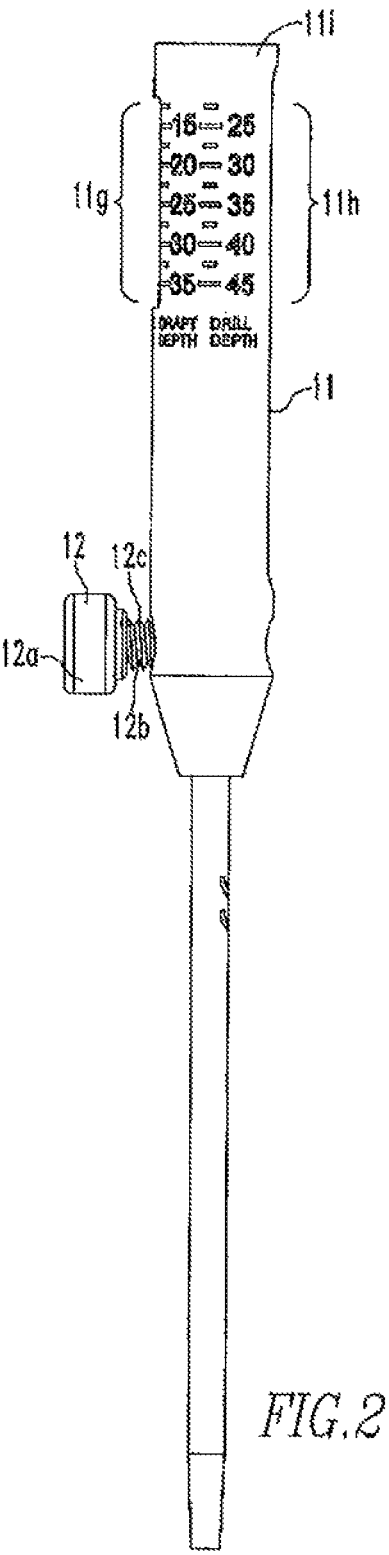
FIG. 2 shows a side elevation of the handle and shaft of the device of the present disclosure.
Figure 3:
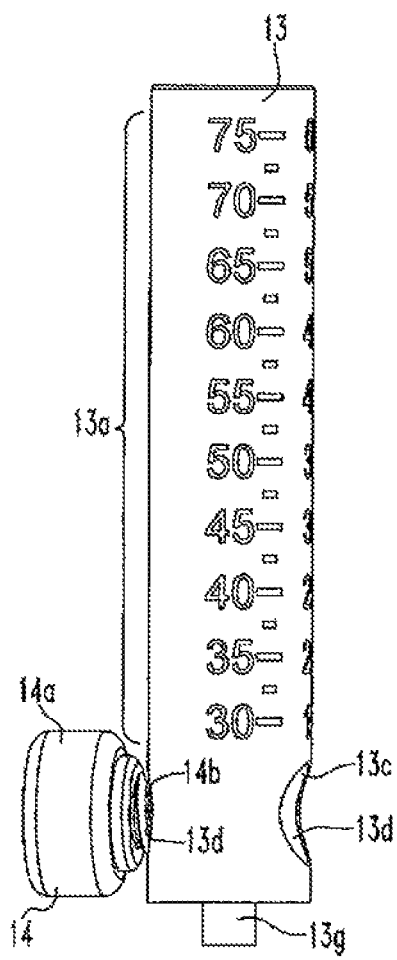
FIG. 3 shows a side elevation of the insert of the device of the present disclosure.
Figure 4:
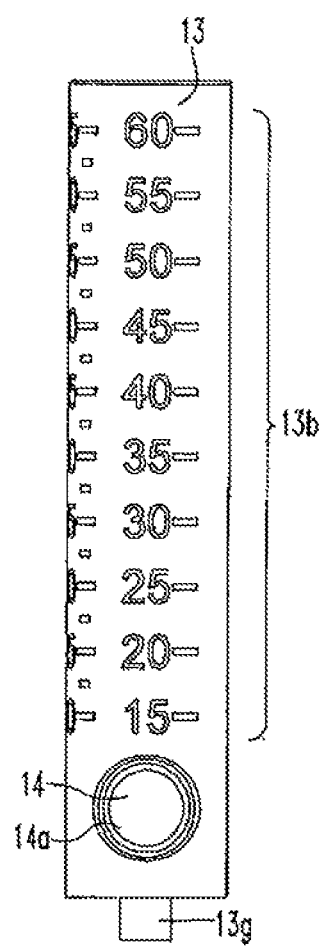
FIG. 4 shows a front elevation of the insert of the device of the present disclosure

FIGS. 1-9 show the device 10 of the present disclosure and/or its components. The device 10 includes a handle 11 and a shaft 11k coupled to the handle 11. The handle 11 includes a first channel 11a having an opening 11a', a second channel 11b having two openings 11b', and a third channel 11c. The second channel 11b is perpendicular to the first and third channels 11a,11c. The handle 11 also includes a first window 11d, a second window 11e, and a groove 11f. A first set of numbers 11g and a second set of numbers 11h are located on the outer surface 11i of the handle 11. The second channel 11b has threads 11j located on an inner surface 11b'' of the second channel 11b. A knob assembly 12 having a knob 12a and a shaft 12b coupled to the knob 12a is coupled to the handle 11 such that the shaft 12b is disposed within the second channel 11b. The shaft 12b includes threads 12c, which engage the threads 11j of the second channel 11b when the shaft 12b is disposed within the second channel 11b. An insert 13, as more clearly shown in FIGS. 3 and 4, is disposed within the first channel 11a. The insert 13 includes a first set of numbers 13a, a second set of numbers 13b, a channel 13c having two openings 13d and threads 13e located on an inner surface 13f of the channel 13c, and a nipple 13g extending from an end of the insert 13. Coupled to the insert 13 is a knob assembly 14 having a knob 14a and a shaft 14b coupled to the knob 14a such that the shaft 14b is disposed within the channel 13c. The shaft 14b includes threads 14c, which engage the threads 13e of the channel 13c when the shaft 14b is disposed within the channel 13c.

When the insert 13 is disposed within the first channel 11a, the shaft 14b is disposed within the groove 11f (FIG. 9), the first set of numbers 13a is shown through the first window 11d, and the second set of numbers 13b is shown through the second window 11e. As will be further described below, the first set of numbers 13a will indicate the required femoral tunnel length and the second set of numbers 13b will indicate the required length of the closed loop of suture that is used with the soft tissue graft. The first set of numbers 11g on the handle 11 serve to indicate the depth of the graft within the femoral bone tunnel, otherwise known as the amount of graft, lengthwise, located in the femoral tunnel, and the second set of numbers 11h serve to indicate the depth in which a surgeon will need to drill to create a femoral socket for the housing of the soft tissue graft.

Figure 10:
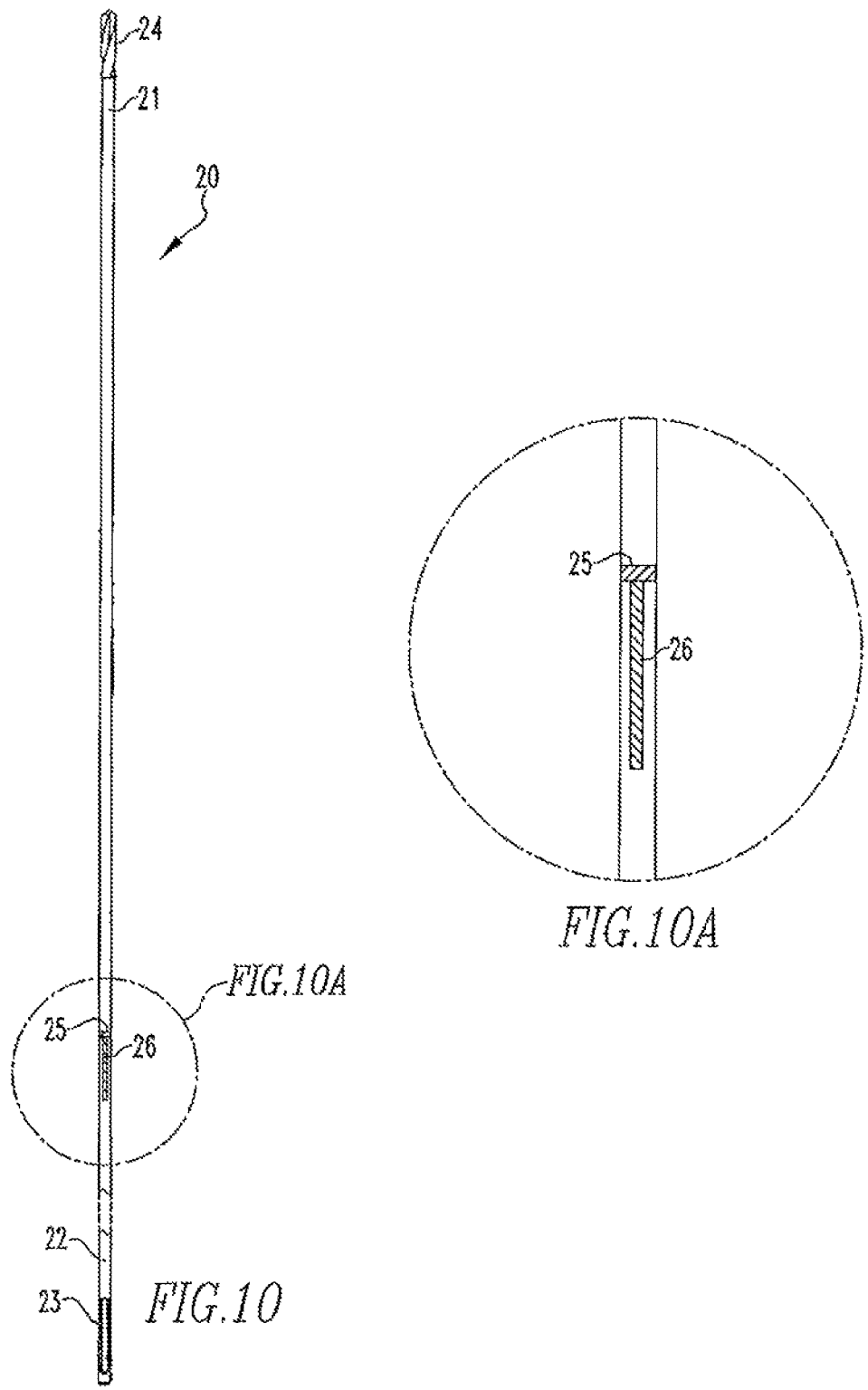

FIG. 10 shows a guide wire 20 having a first end portion 21 and a second end portion 22. The second end portion 22 includes an opening 23 and the first end portion 21 includes grooves 24 for drilling. The guide wire 20 also includes a laser ring 25, as shown in FIG. 10A, located along a length of the guide wire 20 and a laser line 26 extending from the ring 25. The laser ring 25 serves as a reference point for calculations that are taken in preparation for a ligament reconstruction procedure, as will be further described below. For the purposes of this disclosure, the laser ring 25 extends the entire diameter of the guide wire 10. However, the shape and the number of laser marks may vary. It is within the scope of this disclosure to have only the ring 25 located on the wire 20 and not the line 26.

Figure 11:
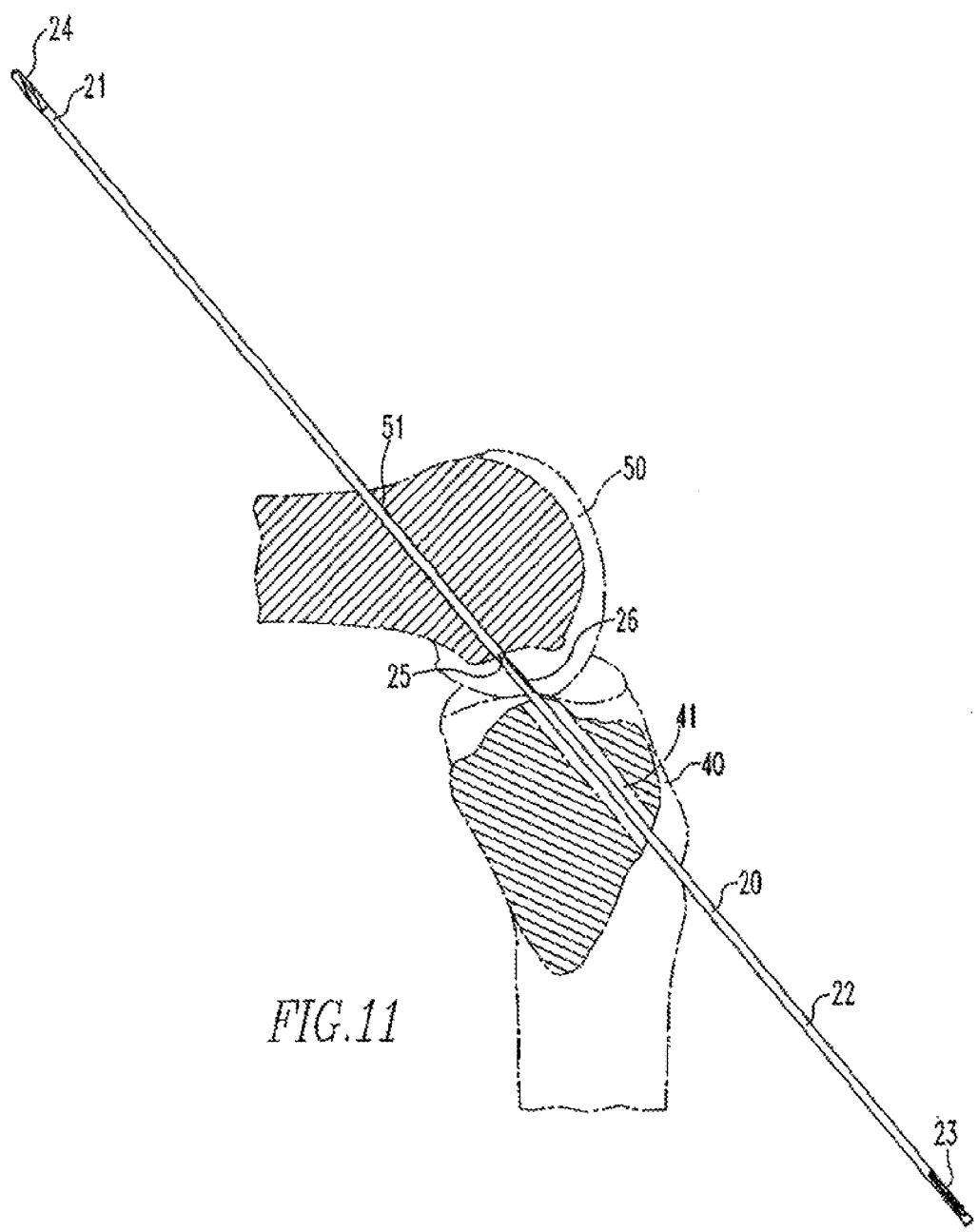
FIG. 11 shows the guidewire deployed at a surgical site.
Figure 12:
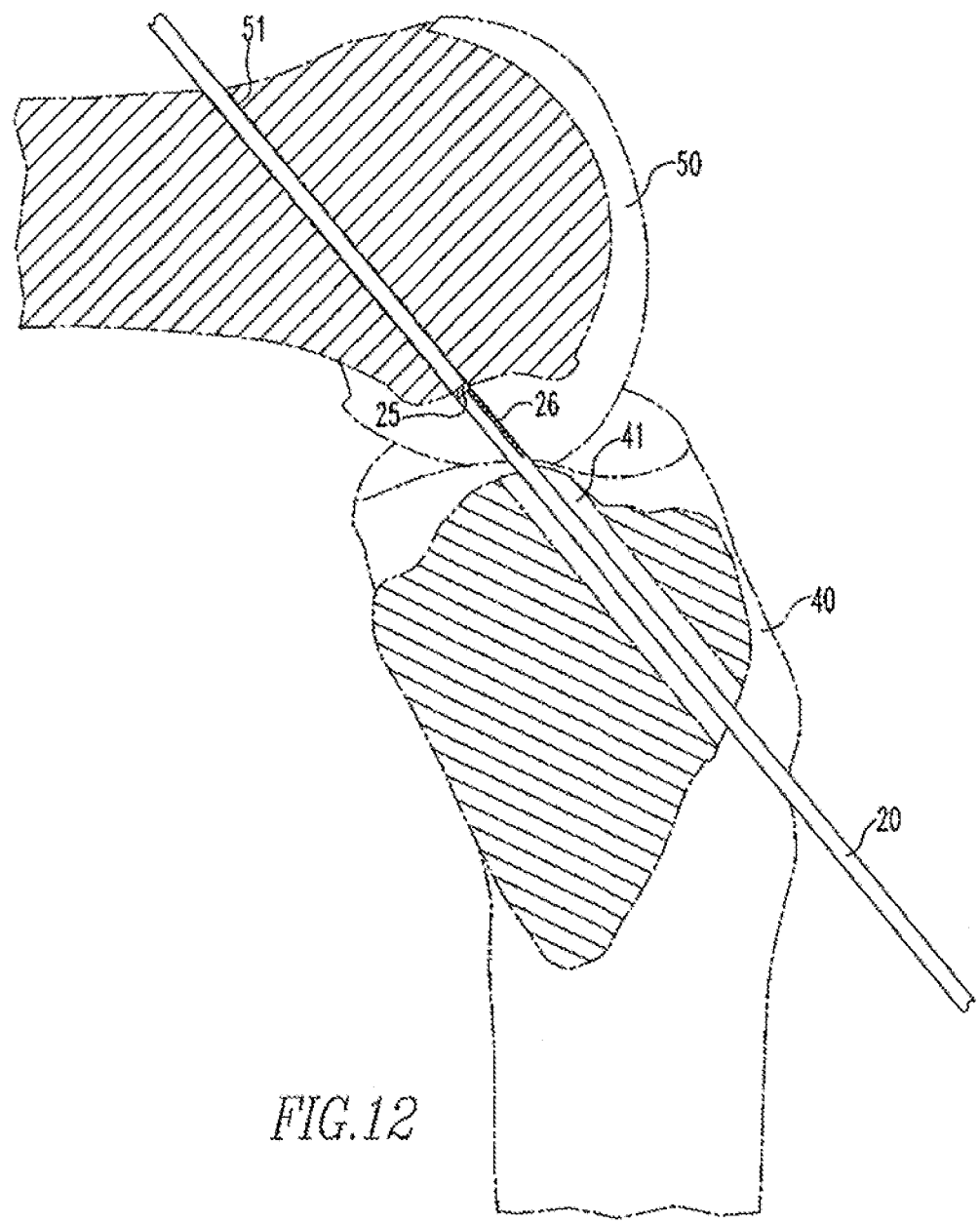
FIG. 12 shows the guidewire deployed and aligned with the femoral notch.

During reconstruction surgery, the knee joint is viewed arthroscopically to determine proper positioning of the femoral and tibial tunnels. In addition, guide systems may be used to position a drill guide along the desired tunnel paths prior to drilling of the tunnels. An example of a guide system is described in U.S. Pat. No. 5,139,520, the disclosure of which is incorporated herein by reference in its entirety. In the present disclosure, after proper positioning of the tunnels has been determined, the tibial tunnel 41 is drilled. Subsequently, the second end 22 of the guide wire 20 is coupled to the drill and the drill is then operated to drill along the desired femoral tunnel path 51, such that the first end 21 of the guide wire 20 extends through the femur 50, as shown in FIG. 11. As mentioned above, the laser ring 25 serves as a reference point for subsequent calculations. Generally, the surgeon will drill through the femur 50 until the laser ring 25 is aligned with an end of the femur 50, more formerly known as the femoral notch, as shown in FIGS. 11 and 12. The laser line 26 serves to let the surgeon know if the surgeon has drilled past the end of the femur 50.

Figure 13:
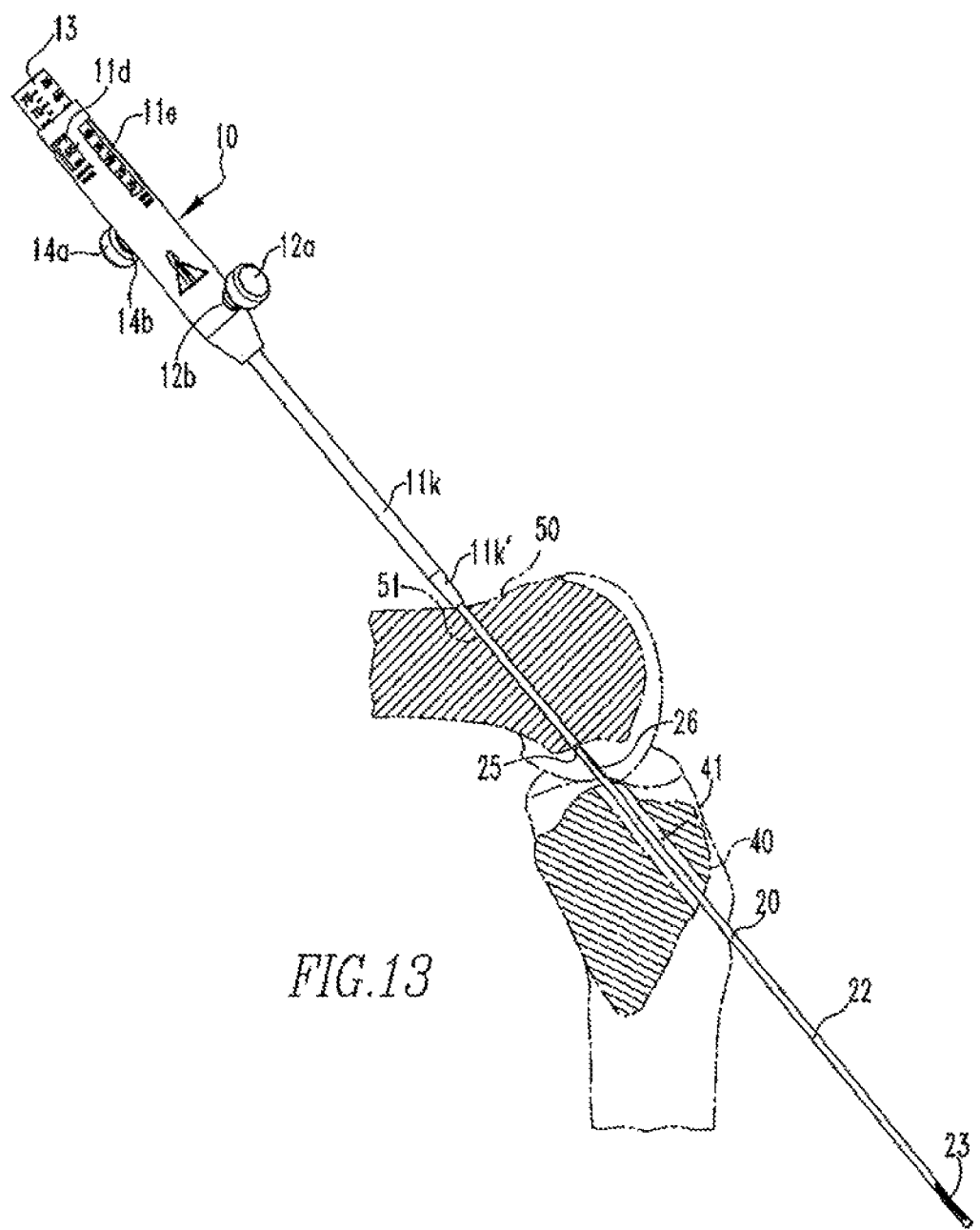
FIG. 13 shows the guidewire deployed through the device at the surgical site.

The device 10 is then placed over the first end 21 of the guide wire 20 such that an end 11k' of the shaft 11k contacts the femur 50, as shown in FIG. 13. Once the device 10 is placed over the first end 21, the end 21 comes into contact with the nipple 13g and moves the insert 13 longitudinally within the handle 11. The knob 12a is rotated so as to engage the shaft 12b with the guide wire 20 and further couple the device 10 to the guide wire 20. Optionally, the knob 14a is rotated to engage the knob 14a and shaft 14b with the handle 11 and further couple the insert 13 to the handle 11.

Next, the surgeon looks in the first window 11d to see what number on the first set of numbers 13a is identified by the hash mark 11l. For instance, FIG. 5 shows the number as being identified as 55. The number identified by the hash mark 11l represents the length the femoral tunnel 54 will be. As will be further described below, the femoral tunnel 54 includes a femoral socket 52 and a through hole 53. Once the femoral tunnel length is identified, the surgeon then chooses the length (L, FIG. 17) for the closed suture loop that will be used and finds this number on the second set of numbers 13b shown through the second window 11e. For the purposes of this disclosure, an Endobutton® Closed Loop (Endobutton® CL) is used to fixate a soft tissue graft within the femoral socket 52. The Endobutton® CL is owned and sold by Smith and Nephew, Inc. and is more fully described within U.S. Pat. No. 6,533,802, which is incorporated herein by reference in its entirety. After the surgeon has chosen a length L for the closed loop suture, the surgeon finds the number on the handle first set of numbers 11g that corresponds with the number that represents the closed loop suture length to determine the graft depth. As stated above, the graft depth is known as the amount of graft, lengthwise, that will be located in the femoral tunnel 54. For instance, as shown in FIG. 6, if the closed loop suture length is 30 mm, the graft depth will be 25 mm.

Figure 7:
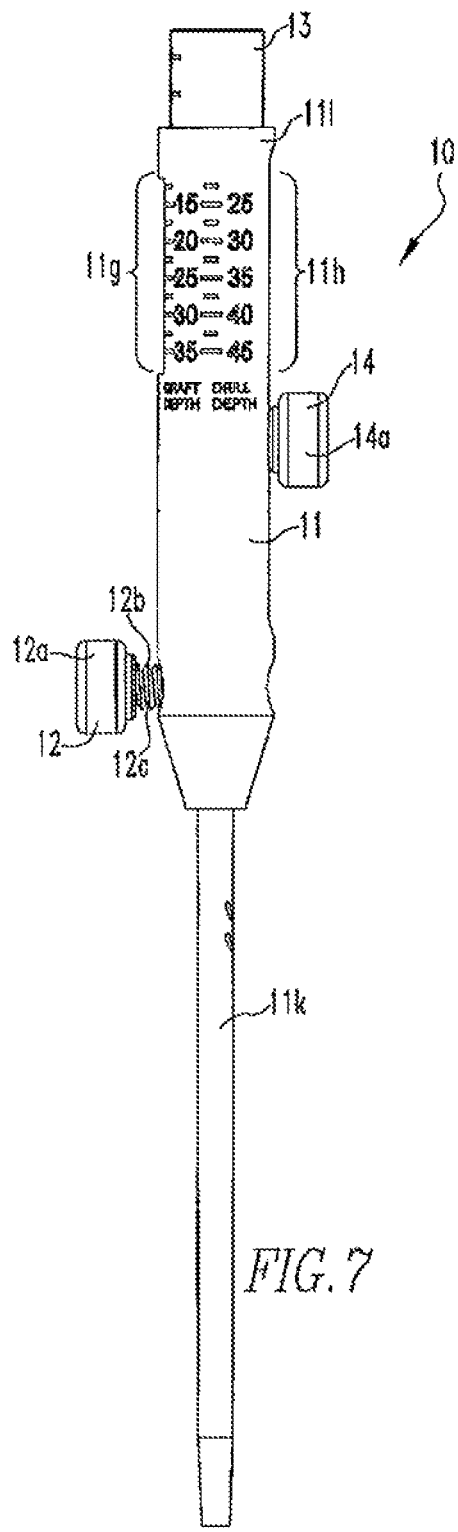
FIG. 7 shows markings visible from another side elevation.
Figure 8:
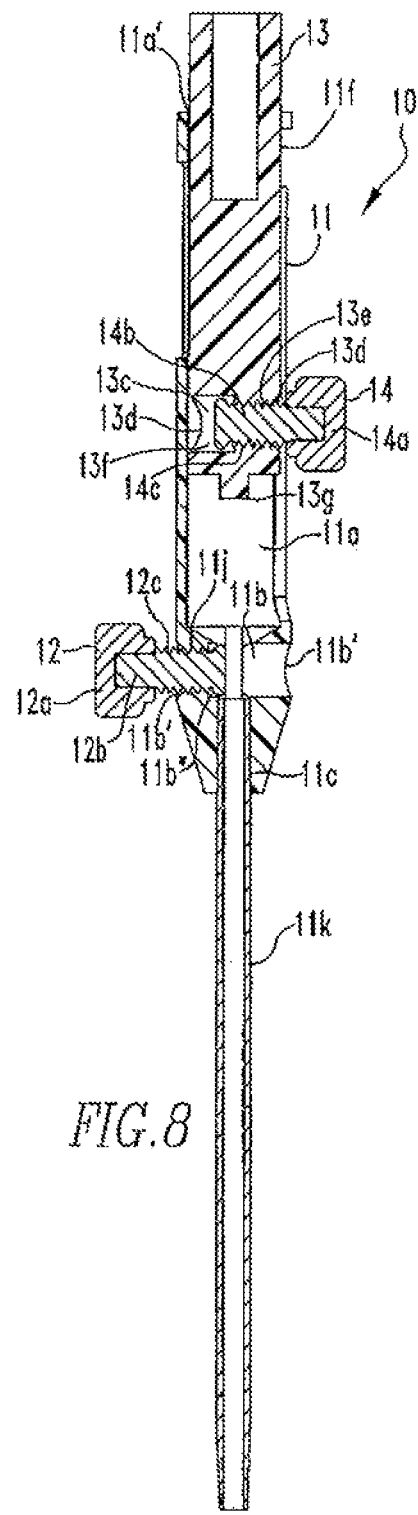
FIG. 8 shows a cross section view of the device of the present disclosure.
Figure 9:
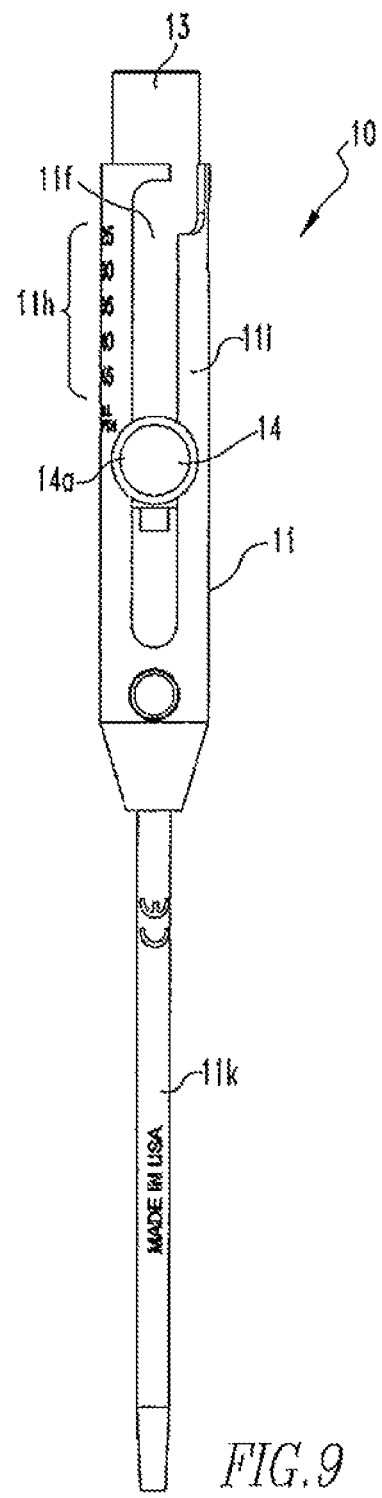
FIG. 9 shows a groove receptive to a shaft of the device.
Figure 14:
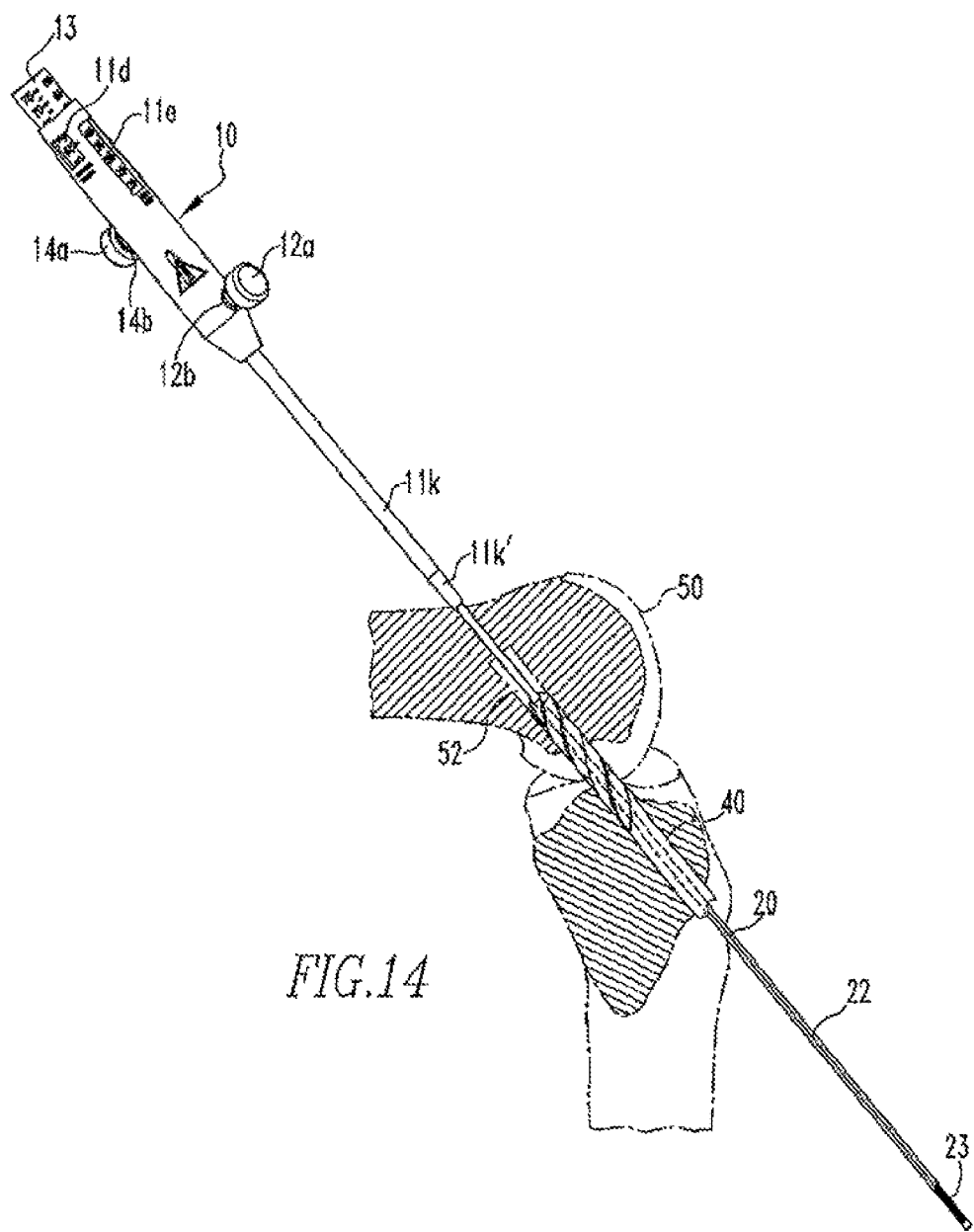
FIG. 14 shows the guidewire at a determined drill depth.

Subsequent to the determination of graft depth, the surgeon will match the number for the graft depth with its corresponding number on the handle second set of numbers 11h to determine the drill depth for the socket 52. For instance, as shown in FIG. 7, if the graft depth is 25 mm, then the drill depth is 35 mm. Once the drill depth is determined, the socket 52 is drilled, as shown in FIG. 14, using the guide wire 20 as a guide. The drill may be marked so that the surgeon knows when the desired depth has been reached.

Figure 15:
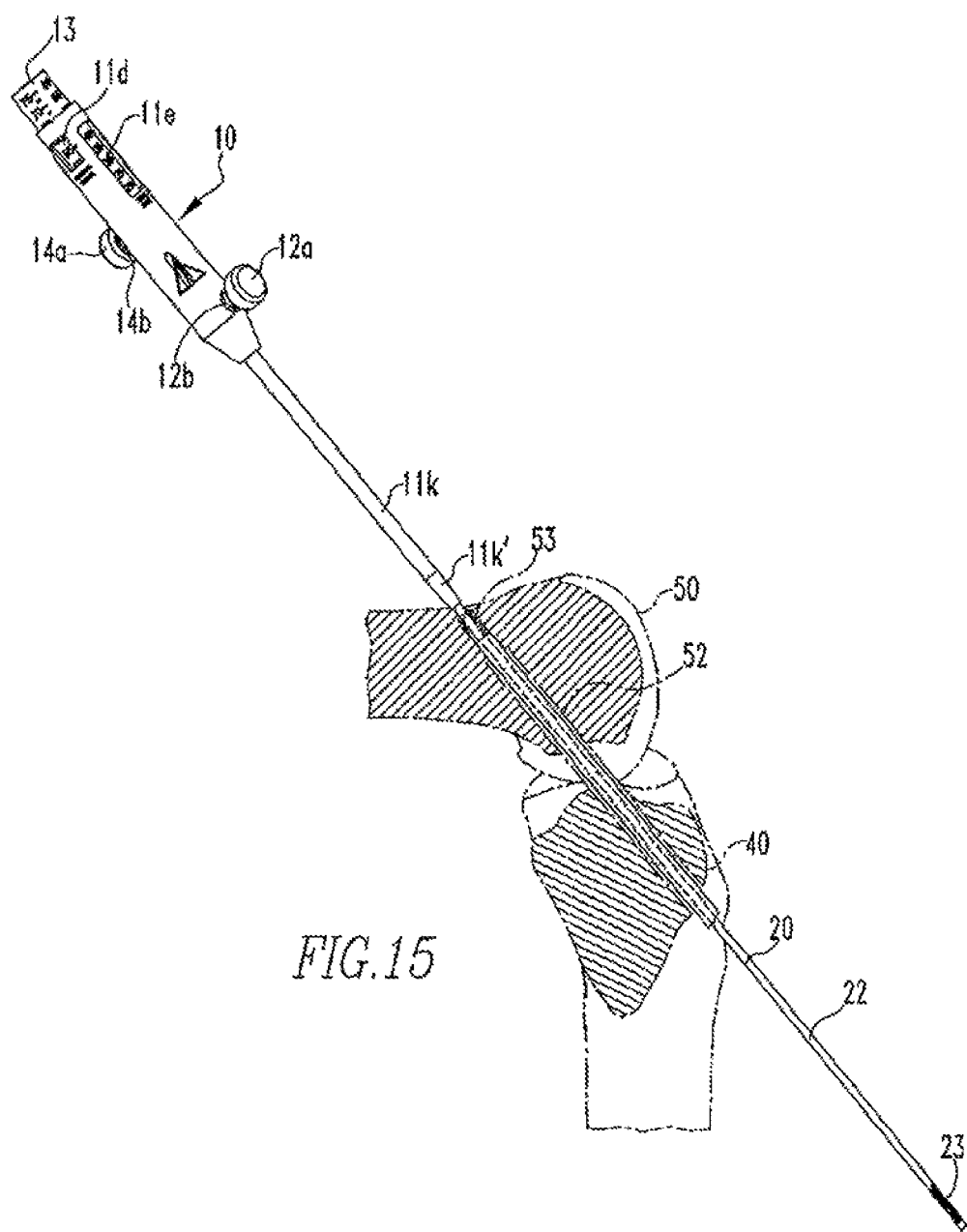
FIG. 15 shows the guidewire used for guiding drilling of a through-hole.

After drilling the socket 52, the surgeon then uses a smaller diameter drill to drill a through hole 53, as shown in FIG. 15. For the purposes of FIG. 15, the drill is not shown as extending through the femur 50. However, in practice the drill will extend through the femur to create through hole 53. The through hole 53 is created to allow for flipping of the Endobutton® device once it is pulled through the tunnel 54, as is described further below. Additionally, the through hole 53 is used to house an amount or length of closed loop suture that extends between the Endobutton® device and the soft tissue graft when the soft tissue graft is housed within the femur 50, as will be further described later.

Figure 16:
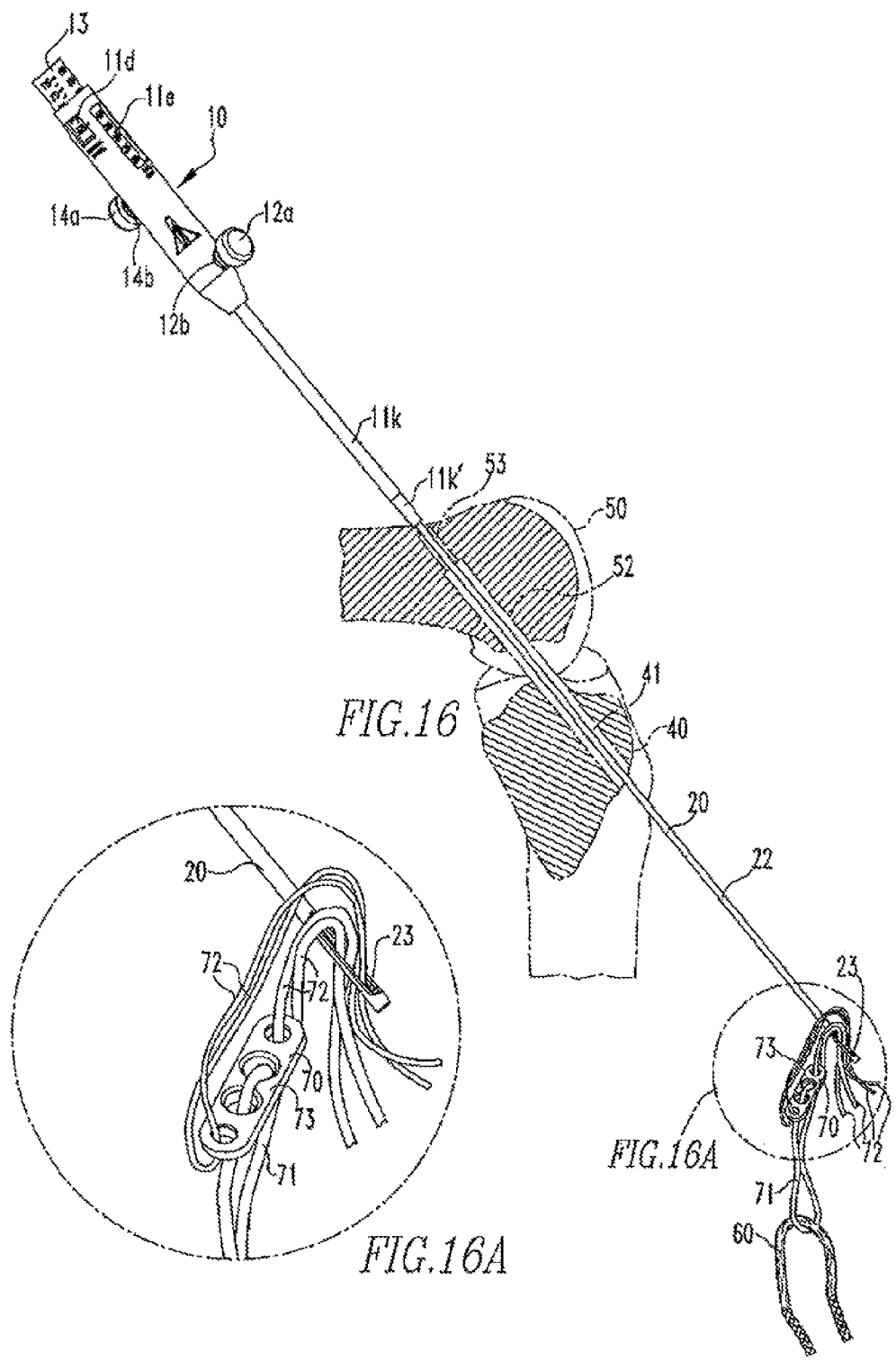
Figure 17:
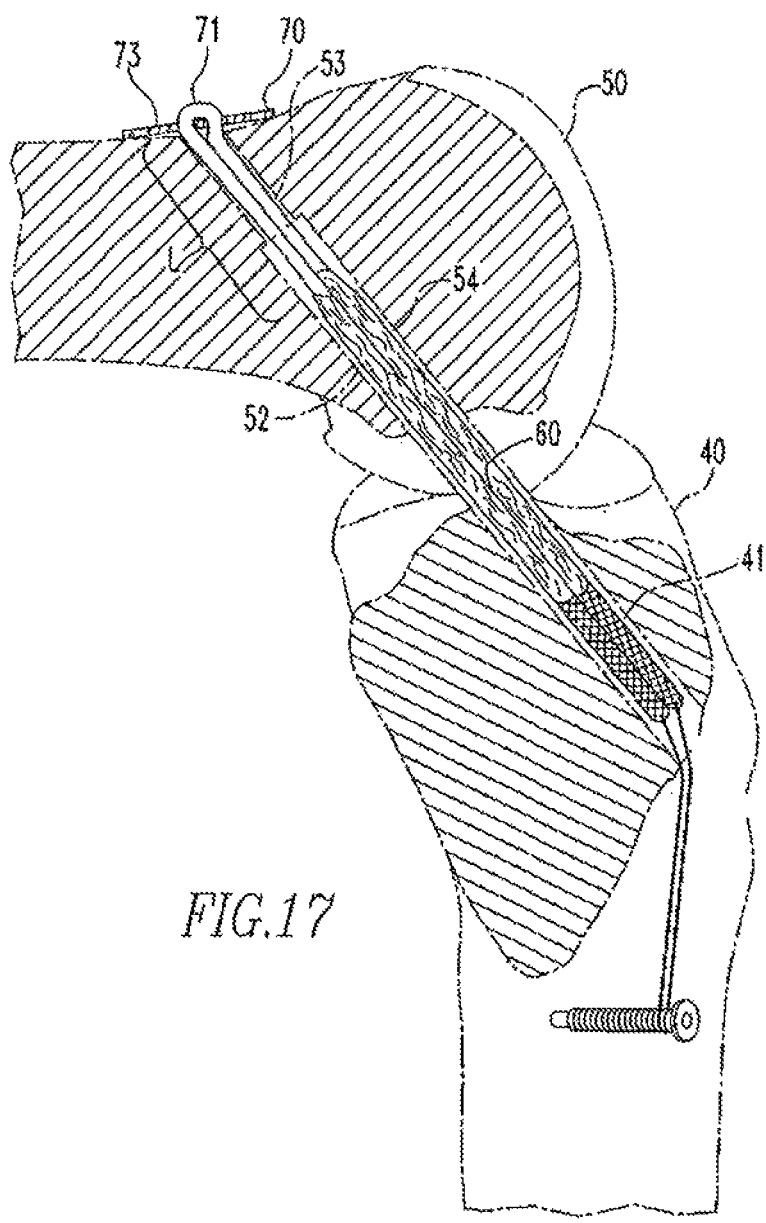
FIG. 17 shows coupling a graft via the suture strand.

Next, the soft tissue graft 60 is coupled to the a fixation device, such as an Endobutton® CL 70, by placing one end of the graft 60 through the closed loop of suture 71 and passing other suture strands 72, connected to the Endobutton® device 73 through the opening 23 of the guide wire 20, as shown in FIGS. 16 and 16A. The soft tissue graft 60 is pulled into the femoral socket 52 and the tibial tunnels 41 via use of the device 10 and the guide wire 20. The suture strands 72 are then used to pull, usually by hand, the Endobutton® device 73 through the through hole 53 and out of the femur 50. Once the Endobutton® device 73 has been pulled out of the femur 50, the device 73 is flipped, such that the device 73 lays across the opening to the through hole 53 and against the femur 50, as shown in FIG. 17. Once the graft 60 has been coupled to the femur 50, the other end of the graft 60 may be coupled to the tibia 40 to finish the procedure, as also shown in FIG. 17.

The guide wire 20 includes a biocompatible metal material, such as stainless material or titanium alloy. The opening 23 may be made via a punch press or other process and the grooves 24 and ring 25/line 26 may be made by a machining or engraving process. The components of the device 10 (handle 11, shaft 11k, insert 13, and knob assemblies 12,14) may also include a biocompatible metal material, such as a stainless steel or titanium alloy, and may be made from a molding or machining process. The first and second set of markings 11g,11h,13a,13b may be made by a process, including, but not limited to, a machining or engraving process and the windows 11d-11e/groove 11f may be made by a process, including, but not limited to, a punch press. It is also within the scope of this disclosure for the insert 13 to not have a nipple 13g extending from its end. During repair, the end 21 of the guide wire 20 would come into contact with the end of the insert 13, rather than the nipple 13g, and move the insert 13 longitudinally within the handle 11.

The device 10 of the present disclosure allows for calculation of the femoral tunnel length, the drill depth of the femoral socket 52, and the graft depth, thereby eliminating the need to perform manual calculations. In addition, the device can be used to safely remove the guide wire 20 from the tibial and femoral tunnels 41,54. For the purposes of this disclosure, the femoral socket 52 is drilled first and the through hole 53 is drilled second. However, it is possible for the through hole 53 to be drilled first and the femoral socket 52 to be drilled second. Also for the purposes of this disclosure, the graft 60 is coupled to the tibia 40 in the manner shown in FIG. 17. However, other manners of coupling the graft 60 to the tibia 40 may be used. Additionally, for the purposes of this disclosure, the shaft 11k is coupled to the handle 11 via press-fitting the shaft 11k to the handle 11. However, other methods may be used.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An assembly for use during ligament reconstruction surgery, the assembly comprising:

a guide wire, the guide wire including a mark configured for aligning the guide wire with respect to a proximal end of a bone tunnel such that a first end of the guide wire is configured to extend through the bone tunnel and protrude out a distal end thereof thereby defining a protruding portion of the guide wire;

a measurement device, the measurement device including a handle and a shaft coupled to the handle, the measurement device being configured to receive and translate over the protruding portion of the guide wire until a distal end of the shaft contacts the distal end of the bone tunnel; and an insert, separate from the guide wire, disposed within a channel of the measurement device and translatable within the channel relative to a first window of the measurement device, the insert including a first set of numbers defined thereon, the first set of numbers configured for display through the first window of the measurement device, the first set of numbers scaled to indicate a range of possible tunnel lengths of the bone tunnel;

wherein the protruding portion of the guide wire is receivable within the measurement device by insertion of the first end of the guide wire through an opening at the distal end of the shaft;

wherein the measurement device is configured so that, when the guide wire is inserted through the bone tunnel and the mark is aligned with the proximal end of the bone tunnel and when the protruding portion of the guide wire is received within the measurement device and the measurement device is translated over the protruding portion of the guide wire until the distal end of the shaft contacts the distal end of the bone tunnel, the guide wire cooperates with the measurement device to indicate a selection from the first set of numbers in the first window indicative of the tunnel length of the bone tunnel; and wherein a distal end of the insert is configured to be contacted by the protruding portion of the guide wire when the protruding portion of the guide wire is received in the measurement device, whereby translating the measurement device over the protruding portion of the guide wire results in the insert being displaced by the guide wire and translated relative to the first window, whereby the selection from the first set of numbers indicative of the tunnel length of the bone tunnel is indicated in the first window.

2. The assembly of claim 1, wherein the distal end of the insert includes a nipple, the nipple configured to contact the first end of the guide wire when the protruding portion of the guide wire is received in the measurement device.

3. The assembly of claim 1, further comprising a locking mechanism for locking a position of the insert within the channel.

4. The assembly of claim 1, wherein the handle includes a groove extending longitudinally along an outer surface of the handle wherein a projection extending laterally from the insert is disposed within the groove and configured to slide along a length of the groove, the projection being provided by a knob assembly, the knob assembly including a knob and a shaft extending from the knob, wherein a threaded end portion of the shaft of the knob assembly extends through the groove in the handle and is disposed within a threaded channel defined in the insert, such that rotating the knob to reduce the distance between the insert and the knob is configured to compress the knob against the handle so as to selectively enable locking the insert relative to the handle.

5. The assembly of claim 1, wherein the insert further includes a second set of numbers for display through a second window of the measurement device, the second set of numbers scaled to indicate a range of possible lengths of a closed loop suture for ligament reconstruction surgery, whereby the measurement device is configured so that the protruding portion of the guide wire, when received in the measurement device, also cooperates to translate the insert relative to the second window so that a selection of a subset of the second set of numbers is indicated in the second window indicative of a range of acceptable lengths of the closed loop suture correlated for use with the tunnel length indicated by the selection from the first set of numbers.

6. The assembly of claim 5, wherein the first window is a non-contiguous with the second window.

7. The assembly of claim 5, wherein the first set of numbers is longitudinally aligned at a first radial position around a perimeter of the insert and the second set of numbers is longitudinally aligned at a second radial position around the perimeter of the insert different from the first radial position.

8. The assembly of claim 5, wherein the first window faces a different radial direction than the second window.

9. The assembly of claim 5 wherein the assembly further includes a third set of numbers in fixed spatial alignment relative to the second window during the translation of the insert and scaled to indicate a range of possible graft depths, wherein the spatial alignment of the third set of numbers relative to the second window correlates each of the numbers in the indicated selection of the subset of the second set of numbers to a corresponding graft depth from the third set of numbers.

10. A method for using the assembly of claim 1, the method comprising:
   inserting the guide wire through the bone tunnel so as to align the mark with respect to the proximal end of the bone tunnel;
   placing the measurement device over the protruding portion of the guide wire so that the protruding portion of the guide wire is received within the measurement device and translating the measurement device over the protruding portion of the guide wire until the distal end of the shaft contacts the distal end of the bone tunnel, thereby displacing the insert;
   reading the selection of the subset of the second set of numbers to ascertain the range of acceptable lengths of the closed loop suture for use with the tunnel length indicated by the selection from the first set of numbers;
   selecting a length of the closed loop suture from the range of acceptable lengths of the closed loop suture; and
   reading the third set of numbers to determine the corresponding graft depth for the selected length of the closed loop suture.

11. The method of claim 10, further comprising using the selected length of closed loop suture to attach a soft tissue graft to the tunnel at the corresponding graft depth.

12. A method for using the assembly of claim 5, the method comprising:
   inserting the guide wire through the bone tunnel so as to align the mark with respect to the proximal end of the bone tunnel;
   placing the measurement device over the protruding portion of the guide wire so that the protruding portion of the guide wire is received within the measurement device and translating the measurement device over the protruding portion of the guide wire until the distal end of the shaft contacts the distal end of the bone tunnel, thereby displacing the insert;
   reading the selection of the first set of numbers through the first window to ascertain the tunnel length of the bone tunnel; and
   reading the selection of the subset of the second set of numbers to ascertain the range of acceptable lengths of the closed loop suture for use with the tunnel length indicated by the selection from the first set of numbers.

13. A method for using the assembly of claim 1, the method comprising:
   inserting the guide wire through the bone tunnel so as to align the mark with respect to the proximal end of the bone tunnel;
   placing the measurement device over the protruding portion of the guide wire so that the protruding portion of the guide wire is received within the measurement device and translating the measurement device over the protruding portion of the guide wire until the distal end of the shaft contacts the distal end of the bone tunnel, thereby displacing the insert; and
   reading the selection of the first set of numbers through the first window to ascertain the tunnel length of the bone tunnel.

14. An assembly for use during ligament reconstruction surgery, the assembly comprising:
   a guide wire, the guide wire including a mark configured for aligning the guide wire with respect to a proximal end of a bone tunnel such that a first end of the guide wire is configured to extend through the bone tunnel and protrude out a distal end thereof thereby defining a protruding portion of the guide wire; and
   a measurement device, the measurement device including a handle and a shaft coupled to the handle, the measurement device being configured to receive and translate over the protruding portion of the guide wire until a distal end of the shaft contacts the distal end of the bone tunnel;
   wherein the assembly defines a first set of numbers configured for display through a first window of the measurement device, the first set of numbers scaled to indicate a range of possible tunnel lengths of the bone tunnel;
   wherein the assembly defines a second set of numbers configured for display through a second window of the measurement device, the second set of numbers scaled to indicate a range of possible lengths of a closed loop suture for ligament reconstruction surgery;
   wherein the protruding portion of the guide wire is receivable within the measurement device by insertion of the first end of the guide wire through an opening at the distal end of the shaft;
   wherein the measurement device is configured so that, when the guide wire is Inserted through the bone tunnel and the mark is aligned with the proximal end of the bone tunnel and when the protruding portion of the guide wire is received within the measurement device and the measurement device is translated over the protruding portion of the guide wire until the distal end of the shaft contacts the distal end of the bone tunnel, the guide wire cooperates with the measurement device to indicate a selection from the first set of numbers in the first window indicative of the tunnel length of the bone tunnel; and
   wherein the measurement device is configured so that, when the guide wire is Inserted through the bone tunnel and the mark is aligned with the proximal end of the bone tunnel and when the protruding portion of the guide wire is received within the measurement device and the measurement device is translated over the protruding portion of the guide wire until the distal end of the shaft contacts the distal end of the bone tunnel, the guide wire cooperates with the measurement device to indicate a selection of a subset of the second set of numbers in the second window indicative of a range of acceptable lengths of the closed loop suture correlated for use with the tunnel length indicated by the selection from the first set of numbers.

* * * * *